US012700158B2

(12) United States Patent
Kim et al.

(10) Patent No.: US 12,700,158 B2
(45) Date of Patent: Aug. 4, 2026

(54) IMAGE RECONSTRUCTION SYSTEM AND METHOD FOR OUTPUTTING 3D SYNTHESIZED IMAGE FROM 2D X-RAY IMAGE BASED ON ARTIFICIAL INTELLIGENCE

(71) Applicant: UIF (University Industry Foundation), Yonsei University, Seoul (KR)

(72) Inventors: Hyoungsik Kim, Yongin-si (KR); Dukyong Yoon, Suwon-si (KR); Jinsik Yoon, Hwaseong-si (KR)

(73) Assignee: UIF (UNIVERSITY INDUSTRY FOUNDATION), YONSEI UNIVERSITY, Seoul (KR)

( * ) Notice: Subject to any disclaimer, the term of this patent is extended or adjusted under 35 U.S.C. 154(b) by 169 days.

(21) Appl. No.: 18/770,856

(22) Filed: Jul. 12, 2024

(65) Prior Publication Data

US 2025/0356545 A1     Nov. 20, 2025

(30) Foreign Application Priority Data

May 16, 2024     (KR) ........................ 10-2024-0063664

(51) Int. Cl.
*G06T 12/00*     (2026.01)
*G06N 3/02*     (2006.01)
(Continued)

(52) U.S. Cl.
CPC ................ *G06T 12/10* (2026.01); *G06T 7/12* (2017.01); *G06T 15/00* (2013.01); *G16H 30/40* (2018.01); *G06T 2207/10116* (2013.01)

(58) Field of Classification Search
USPC .............................. 382/1–132, 155–156, 159
See application file for complete search history.

(56) References Cited

U.S. PATENT DOCUMENTS

| | | | | |
|---|---|---|---|---|
| 10,380,736 B1 * | 8/2019 | Partain | ...................... | G06T 7/11 |
| 10,867,436 B2 * | 12/2020 | Oved | ........................ | G06T 7/50 |

(Continued)

FOREIGN PATENT DOCUMENTS

| | | |
|---|---|---|
| JP | 2022-505587 | 1/2022 |

OTHER PUBLICATIONS

Arya et al., Generation of Pseudo X-ray and Digitally Reconstructed Radiograph from CT images, 2025IEEE 978-8-3315, pp. 2150-2154 . (Year: 2025).*

(Continued)

*Primary Examiner* — Ishrat I Sherali
(74) *Attorney, Agent, or Firm* — LEX IP MEISTER, PLLC

(57)     ABSTRACT

Disclosed herein is an image reconstruction system for outputting a three-dimensional (3D) synthesized image from a two-dimensional (2D) X-ray image based on artificial intelligence, the image reconstruction system including: an artificial intelligence learning unit configured such that a correct answer 3D image in which bones are segmented and extracted is generated from a sample 3D computed tomography (CT) image, a sample 2D image is generated from the correct answer 3D image, a sample 3D synthesized image is generated from the 2D image, and an artificial intelligence learning model is constructed as the generated sample 3D synthesized image is learned; a Maximum Intensity Projection (MIP) image conversion unit configured such that a target 2D MIP image is generated; and a final 3D synthesized image output unit configured such that the target 2D MIP image is input to the learning model, and thus, a final 3D synthesized image is output.

19 Claims, 23 Drawing Sheets

Artificial Intelligence Learning Unit (100) → MIP Image Conversion Unit (200) → Final 3D Synthesized Image Output Unit (300)

(51) Int. Cl.

| | |
|---|---|
| *G06T 7/12* | (2017.01) |
| *G06T 12/10* | (2026.01) |
| *G06T 15/00* | (2011.01) |
| *G16H 30/40* | (2018.01) |

(56)                    References Cited

U.S. PATENT DOCUMENTS

| | | | |
|---|---|---|---|
| 11,615,560 B2 * | 3/2023 | Chen ...................... | A61B 6/487 |
| | | | 382/128 |
| 2016/0270853 A1 * | 9/2016 | Lavallee ................. | A61F 2/389 |
| 2020/0334897 A1 * | 10/2020 | Oved ........................ | G06T 7/50 |
| 2025/0014177 A1 * | 1/2025 | Vöth ...................... | G06T 7/0012 |

OTHER PUBLICATIONS

Reyneke et al., Review of 2-D/3-D Reconstruction Using Statistical Sape and Intensity Models and X-Ray Image Synthesis: Toward a Unified Framework, 2018IEEE 1973-3333, IEEE Reviews in Biomedical Engineering, vol. 12, 2019, pp. 269-286. (Year: 2019).*

Eva Milara et al., "Automatic Skeleton Segmentation in CT Images Based on U-Net", Journal of Imaging Informatics in Medicine (2024) 37:2390-2400, Apr. 30, 2024.

Kim, Jong Gi et al., "Standardization of MIP Technique in Three-dimensional CT Portography: Usefulness in Evaluation of Portosystemic Collaterals in Cirrhotic Patients", Journal of the Korean Radiological Society, vol. 49, Issue 2, Aug. 2003, pp. 99-105, doi:10.3348/jkrs.2003.49.2.99.

KIPO, Office Action of KR 10-2024-0063664 dated May 21, 2026, total 22 pages.

* cited by examiner

Artificial Intelligence Learning Unit(100)

Data Input Unit (110)

Bone Segmentation and Extraction Unit (120)

Sample 2D Image Generation Unit (130)

Learning Model Construction Unit (140)

(A1) 3D image (A3) 3D image

FIG. 15

In artificial intelligence learning unit, correct answer 3D image in which bones are segmented and extracted is generated from sample 3D computed tomography (CT) image, sample 2D image is generated from correct answer 3D image, sample 3D synthesized image is generated from 2D image, and artificial intelligence learning model is constructed as generated sample 3D synthesized image is learned by being compared with the correct answer 3D image    ~S100

In MIP image conversion unit, input target 2D X-ray image and sample 2D image are input to preset learning model, and thus, target 2D MIP image is generated    ~S200

In final 3D synthesized image output unit, target 2D MIP image generated in MIP image conversion unit is input to learning model constructed in artificial intelligence learning unit, and thus, final 3D synthesized image is output    ~S300

IMAGE RECONSTRUCTION SYSTEM AND METHOD FOR OUTPUTTING 3D SYNTHESIZED IMAGE FROM 2D X-RAY IMAGE BASED ON ARTIFICIAL INTELLIGENCE

CROSS-REFERENCE TO RELATED APPLICATION

This application claims the benefit of Korean Patent Application No. 10-2024-0063664 filed on May 16, 2024, which is hereby incorporated by reference herein in its entirety.

BACKGROUND

1. Technical Field

The present invention generally relates to an image reconstruction system and method. More particularly, the present invention relates to an image reconstruction system and method for outputting a three-dimensional (3D) synthesized image from a two-dimensional (2D) X-ray image based on artificial intelligence.

2. Description of the Related Art

Deep learning algorithms that receive 2D images of an object taken from multiple directions and reconstruct a 3D image include multiple algorithms applying a convolutional neural network (CNN), and are being used in various industrial fields.

In the case of conventional technology for performing three-dimensional reconstruction using human X-ray images, surfaces of bones are synthesized three-dimensionally, but a problem arises in that internal tomography, which is one of the computed tomography (CT) functions, cannot be synthesized. In other words, there are limitations when a user desires to make a determination by observing the insides of bones of a patient. Furthermore, the conventional technology also has the limitation of reconstructing bones having simple shapes rather than objects having complex shapes.

PRIOR ART LITERATURE

Patent Document: Korean Patent Application Publication No. 10-2022-0128505 (published on Sep. 21, 2022)

SUMMARY

An image reconstruction system and method for outputting a 3D synthesized image from a 2D X-ray image based on artificial intelligence according to the present invention have the following objects:

A first object is to, based on artificial intelligence, synthesize a reconstructed 3D stereoscopic image of CT of bones by using one or more 2D plane radiographs (e.g., X-ray images).

A second object is to increase the quality of a synthesized 3D image by using a learning model.

A third object is to overcome the problem in which training is not easily performed because the exact alignment between an X-ray image and a CT image is not achieved.

The objects of the present invention are not limited to those mentioned above, and other objects not mentioned will be clearly understood by those having ordinary skill in the art from the following description.

According to an aspect of the present invention, there is provided an image reconstruction system that is operated by a control server having a database and a computation function and outputs a 3D synthesized image from a 2D X-ray image based on artificial intelligence, the image reconstruction system including: an artificial intelligence learning unit configured such that a correct answer 3D image in which bones are segmented and extracted is generated from a sample 3D CT image, a sample 2D image is generated from the correct answer 3D image, a sample 3D synthesized image is generated from the 2D image, and an artificial intelligence learning model is constructed as the generated sample 3D synthesized image is learned by being compared with the correct answer 3D image; a Maximum Intensity Projection (MIP) image conversion unit configured such that an input target 2D X-ray image and the sample 2D image are input to a preset learning model, and thus, a target 2D MIP image is generated; and a final 3D synthesized image output unit configured such that the target 2D MIP image generated by the MIP image conversion unit is input to the learning model constructed by the artificial intelligence learning unit, and thus, a final 3D synthesized image is output.

The artificial intelligence learning unit may include: a data input unit configured such that the sample 3D CT image is input thereto; a bone segmentation and extraction unit configured such that the correct answer 3D image in which bones are segmented, extracted and reconstructed is generated from the input sample 3D CT image; a sample 2D image generation unit configured such that the sample 2D image is generated from the correct answer 3D image generated in the bone segmentation and extraction unit; and a learning model construction unit configured such that the sample 3D synthesized image is generated from the sample 2D image generated in the sample 2D image generation unit and the artificial intelligence learning model is constructed as the generated sample 3D synthesized image is learned by being compared with the correct answer 3D image.

The bone segmentation and extraction unit may perform operation by using a deep learning segmentation technique.

The deep learning segmentation technique may be any one of image segmentation and semantic segmentation.

The sample 2D image generation unit may perform operation by using an MIP technique.

In the learning model construction unit, the training may be performed using a Generative Adversarial Network (GAN) model.

The MIP image conversion unit may include: a data input unit configured such that the target 2D X-ray image and the sample 2D image are input thereto; and an MIP learning unit configured such that the target 2D X-ray image and sample 2D image input to the data input unit are input to the learning model, and thus, the target 2D MIP image is generated.

In the MIP learning unit, the input target 2D X-ray image may be generated as the target 2D MIP image by an MIP technique.

In the MIP learning unit, the training may be performed using a Cycle GAN model.

According to another aspect of the present invention, there is provided an image reconstruction method that is performed by a control server having a database and a computation function and outputs a 3D synthesized image from a 2D X-ray image based on artificial intelligence, the image reconstruction method including: step S100 configured such that in an artificial intelligence learning unit, a correct answer 3D image in which bones are segmented and extracted is generated from a sample 3D CT image, a sample 2D image is generated from the correct answer 3D image, a sample 3D synthesized image is generated from the 2D image, and an artificial intelligence learning model is constructed as the generated sample 3D synthesized image is learned by being compared with the correct answer 3D image; step S200 configured such that in a Maximum Intensity Projection (MIP) image conversion unit, an input target 2D X-ray image and the sample 2D image are input to a preset learning model, and thus, a target 2D MIP image is generated; and step S300 configured such that in a final 3D synthesized image output unit, the target 2D MIP image generated in the MIP image conversion unit is input to the learning model constructed in the artificial intelligence learning unit, and thus, a final 3D synthesized image is output.

Step S100 may include: step S110 configured such that in a data input unit, the sample 3D CT image is input thereto; step S120 configured such that in a bone segmentation and extraction unit, the correct answer 3D image in which bones are segmented, extracted and reconstructed is generated from the input sample 3D CT image; step S130 configured such that in a sample 2D image generation unit, the sample 2D image is generated from the correct answer 3D image generated in the bone segmentation and extraction unit; and step S140 configured such that in a learning model construction unit, the sample 3D synthesized image is generated from the sample 2D image generated in the sample 2D image generation unit and the artificial intelligence learning model is constructed as the generated sample 3D synthesized image is learned by being compared with the correct answer 3D image.

Step S120 may be performed using a deep learning segmentation technique.

The deep learning segmentation technique may be any one of image segmentation and semantic segmentation.

Step S130 may be performed using an MIP technique.

In step S140, the training may be performed using a Generative Adversarial Network (GAN) model.

Step S200 may include: step S210 configured such that in a data input unit, the target 2D X-ray image and the sample 2D image are input thereto; and step S210 configured such that in an MIP learning unit, the target 2D X-ray image and sample 2D image input to the data input unit are input to the learning model, and thus, the target 2D MIP image is generated.

In step S220, the input target 2D X-ray image may be generated as the target 2D MIP image by an MIP technique.

In step S220, the training may be performed using a Cycle GAN model.

According to still another aspect of present invention, there is provided a computer program stored in a computer-readable storage medium to cause a computer to execute the image reconstruction method of outputting a 3D synthesized image from a 2D X-ray image based on artificial intelligence in combination with hardware.

BRIEF DESCRIPTION OF THE DRAWINGS

The above and other objects, features, and advantages of the present invention will be more clearly understood from the following detailed description taken in conjunction with the accompanying drawings, in which:

FIG. 15 is a flowchart of an image reconstruction method of outputting a 3D synthesized image from a 2D X-ray image based on artificial intelligence according to the present invention.

DETAILED DESCRIPTION

Figures 1, 2:
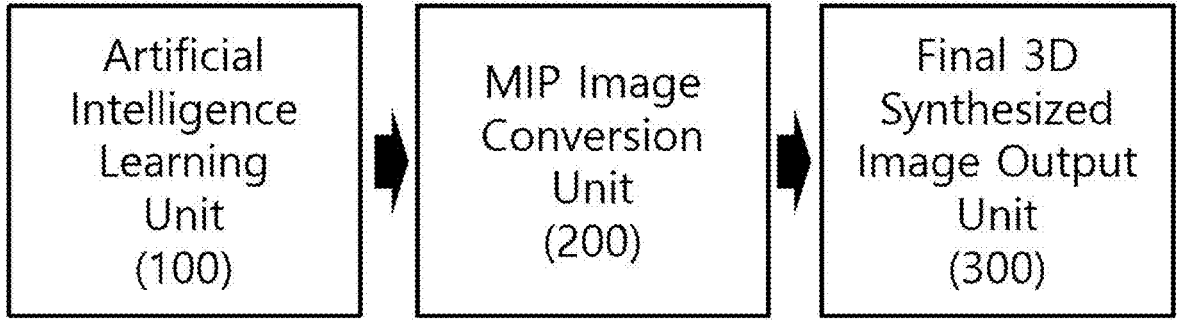
FIG. 1 is a block diagram of an image reconstruction system for outputting a 3D synthesized image from a 2D X-ray image based on artificial intelligence according to the present invention.
FIG. 2 is a block diagram showing the detailed configuration of an artificial intelligence learning unit according to the present invention.

Embodiments of the present invention will be described below with reference to the accompanying drawings so that those having ordinary skill in the art to which the present invention pertains can easily implement the present invention. As can be easily understood by those having ordinary skill in the art to which the present pertains, the embodiments to be described below may be modified into various forms within a range without departing from the concept and scope of the present invention. Identical or similar parts are denoted using the same reference numerals throughout the drawings as much as possible.

The terminology used herein is only intended to refer to specific embodiments and is not intended to limit the invention. As used herein, singular forms include plural forms unless phrases clearly indicate the contrary.

The meaning of "include," "comprise," "including," "comprising," and their derivatives used herein is intended to specify one or more particular characteristics, areas, integers, steps, operations, elements, and/or components, and does not exclude the presence or addition of any other specific characteristic, area, integer, step, operation, element, component, and/or group.

All the terms, including technical and scientific terms, used herein have the same meanings as those generally understood by those having ordinary skill in the art to which the present invention pertains. The terms defined in the dictionary are further interpreted as having meanings consistent with the related technical literature and currently disclosed content, and are not interpreted as having ideal or excessively formal meanings unless defined to the contrary.

The terms used therein and also related to the direction, e.g., front/back/left/right, top/bottom, and vertical/lateral directions, may be interpreted with reference to the directions shown in the drawings.

The present invention is directed to technology for synthesizing a 3D skeletal image, reconstructed in CT by using one or more plain radiographs, by using artificial intelligence.

Through the present invention, a complex anatomical structure or lesion may be visualized more clearly. Accordingly, the present invention may be particularly useful for revealing details that are difficult to determine by using traditional 2D radiographs, such as a bone structure, differences in tissue density, or a small lesion. Furthermore, the present invention may contribute to helping medical staff make more accurate diagnoses and establish effective treatment plans.

In the present specification, A (original) (3D), A1 (3D), A2 (2D), and A3 (3D) each refer to a 3D or 2D image of a third party (a sample). B1 and B2 each refer to a 2D image of a patient (a target) to be analyzed. C1 refers to a 3D image of a patient (a target) generated from a plane X-ray image of the patient.

The present invention will be described below with reference to the accompanying drawings. For reference, the drawings may be partially exaggerated to illustrate features of the present invention. In this case, it is preferable that corresponding portions be interpreted in light of the overall purpose of the present specification.

FIG. 1 is a block diagram of an image reconstruction system for outputting a 3D synthesized image from a 2D X-ray image based on artificial intelligence according to the present invention.

The present invention provides an image reconstruction system that is operated by a control server having a database and a computation function and outputs a 3D synthesized image from a 2D X-ray image based on artificial intelligence, the image reconstruction system including: an artificial intelligence learning unit 100 configured such that a correct answer 3D image A1 in which bones are segmented and extracted is generated from a sample 3D CT image, a sample 2D image A2 is generated from the correct answer 3D image A1, a sample 3D synthesized image A3 is generated from the 2D image A2, and an artificial intelligence learning model is constructed as the generated sample 3D synthesized image A1 is learned by being compared with the correct answer 3D image A1; an MIP image conversion unit 200 configured such that an input target 2D X-ray image B1 and the sample 2D image A2 are input to a preset learning model, and thus, a target 2D MIP image B2 is generated; and a final 3D synthesized image output unit 300 configured such that the target 2D MIP image B2 generated in the MIP image conversion unit 200 is input to the learning model constructed in the artificial intelligence learning unit 100, and thus, a final 3D synthesized image C1 is output.

The artificial intelligence learning unit 100 according to the present invention will be described below.

In the artificial intelligence learning unit 100, the correct answer 3D image A1 in which bones are segmented and extracted may be generated from the sample 3D CT image, the sample 2D image A2 may be generated from the correct answer 3D image A1, the sample 3D synthesized image A3 may be generated from the 2D image A2, and the artificial intelligence learning model may be constructed as the generated sample 3D synthesized image A1 is learned by being compared with the correct answer 3D image A1.

Figure 3:
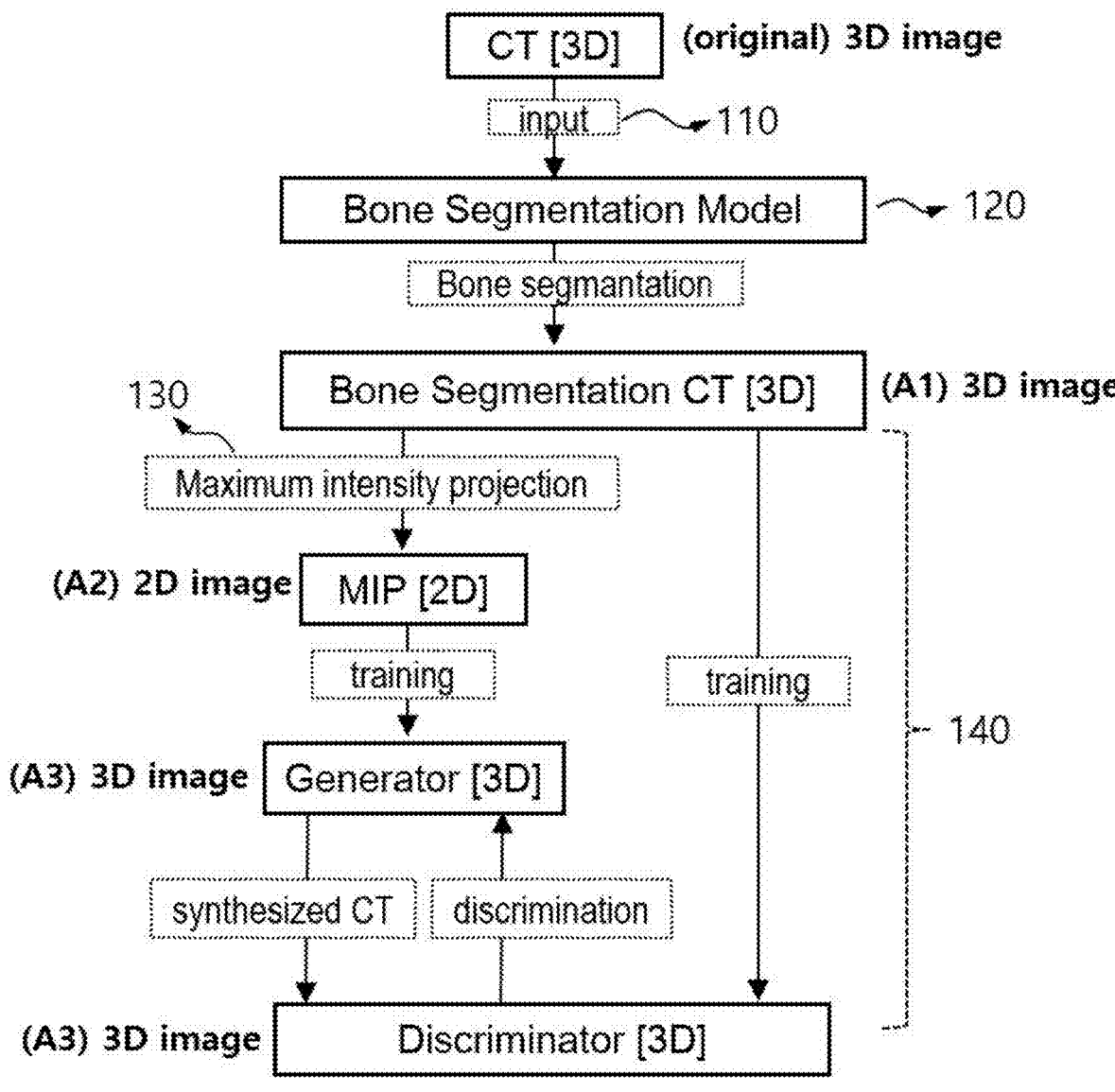
FIG. 3 shows the operating principle of the artificial intelligence learning unit.
Figure 4A:
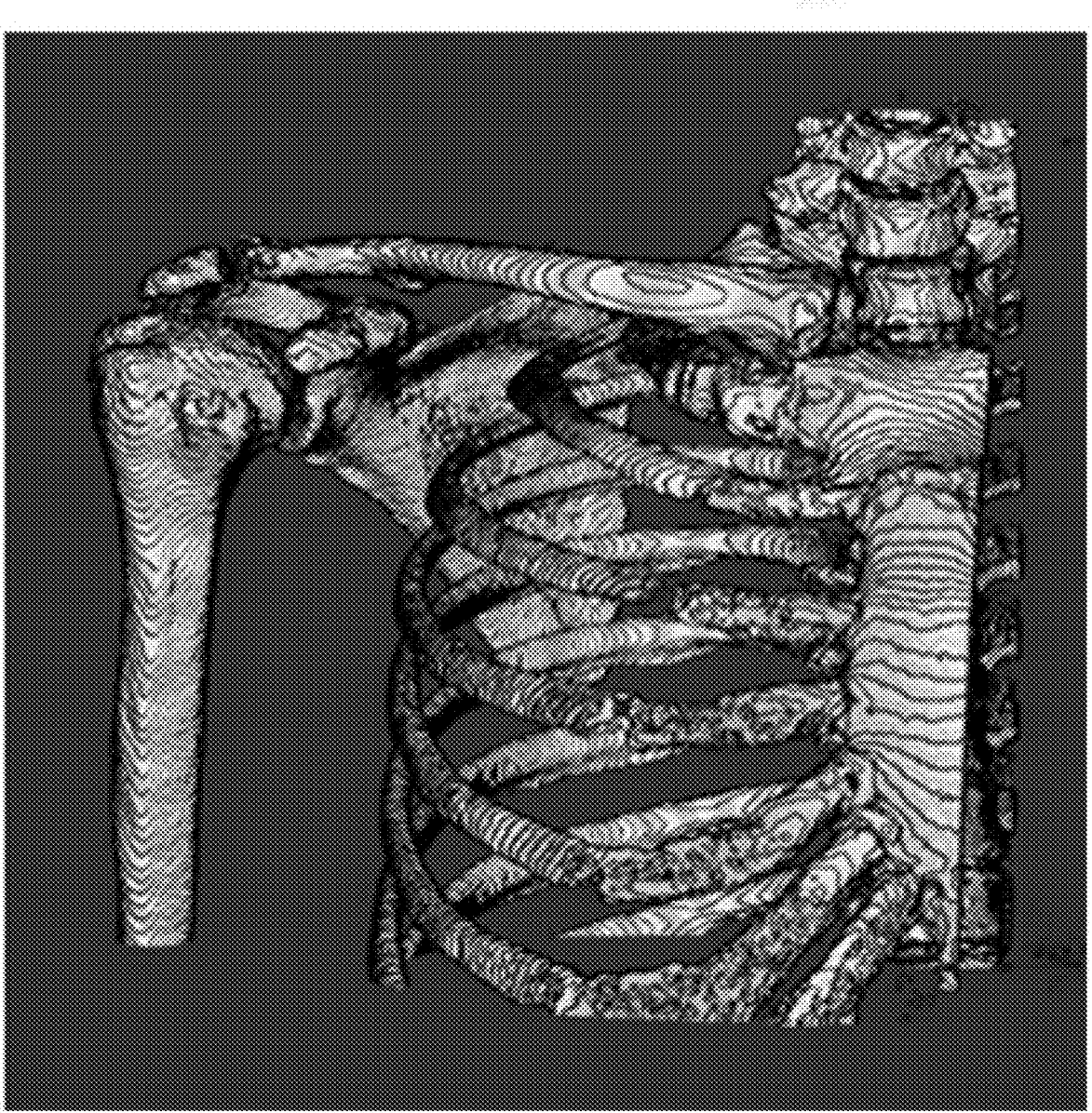
FIG. 4(a) shows a correct answer 3D image in the artificial intelligence learning unit.

FIG. 2 is a block diagram showing the detailed configuration of the artificial intelligence learning unit 100 according to the present invention. FIG. 3 shows the operating principle of the artificial intelligence learning unit 100. FIG. 4(a) shows the correct answer 3D image A1 in the artificial intelligence learning unit 100, FIG. 4(b) shows the sample 2D image A2, and FIG. 4(c) shows the sample 3D synthesized image A3.

As shown in FIGS. 2 and 3, the artificial intelligence learning unit 100 may include a data input unit 110, a bone segmentation and extraction unit 120, a sample 2D image generation unit 130, and a learning model construction unit 140.

More specifically, the artificial intelligence learning unit 100 may include: the data input unit 110 configured such that the sample 3D CT image is input thereto; the bone segmentation and extraction unit 120 configured such that the correct answer 3D image A1 in which bones are segmented, extracted and reconstructed is generated from the input sample 3D CT image; the sample 2D image generation unit 130 configured such that the sample 2D image A2 is generated from the correct answer 3D image A1 generated in the bone segmentation and extraction unit 120; and the learning model construction unit 140 configured such that the sample 3D synthesized image A3 is generated from the sample 2D image A2 generated in the sample 2D image generation unit 130 and the artificial intelligence learning model is constructed as the generated sample 3D synthesized image A3 is learned by being compared with the correct answer 3D image A1.

Figure 4B:
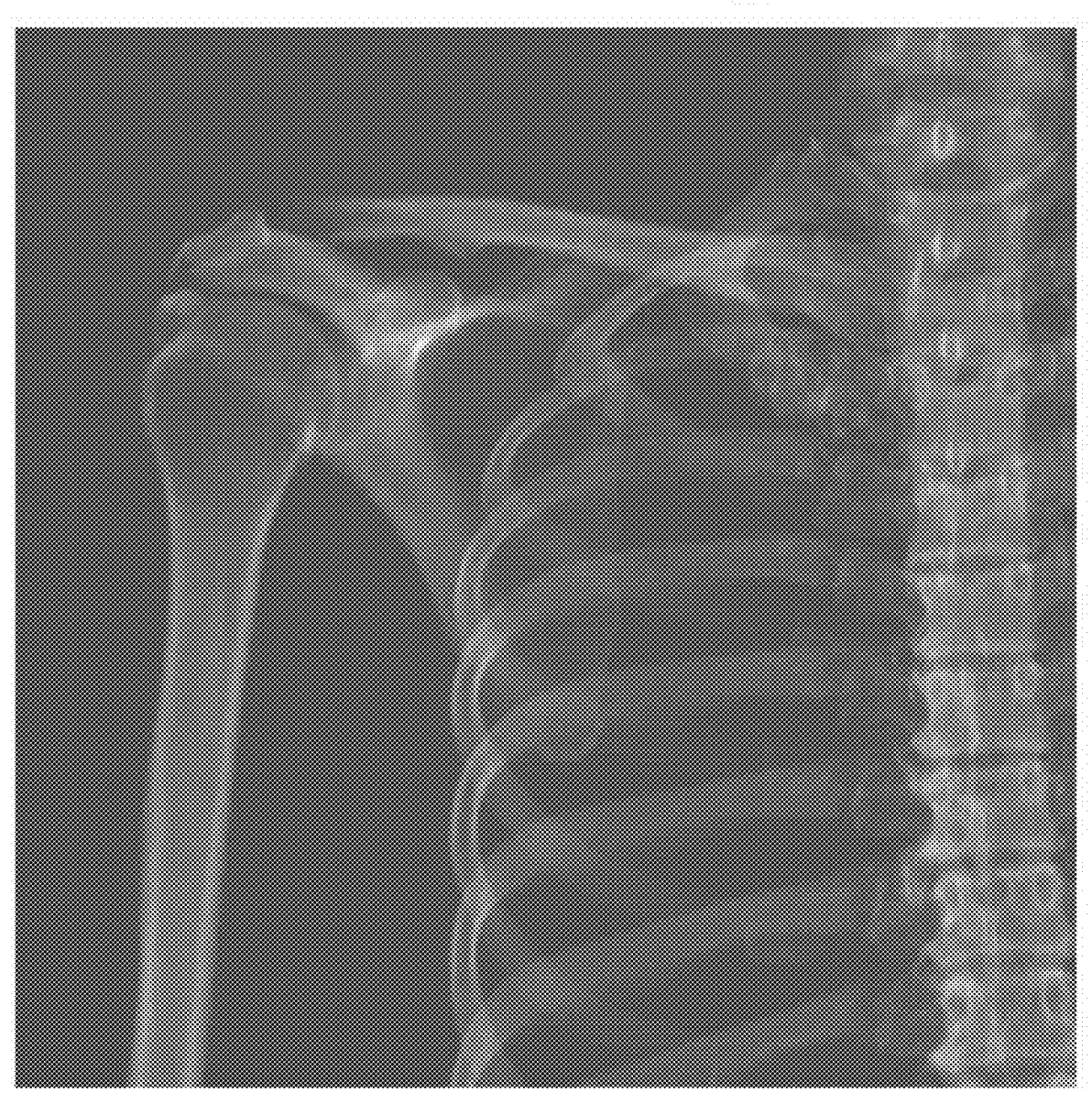
FIG. 4(b) shows a sample 2D image.
Figure 4C:
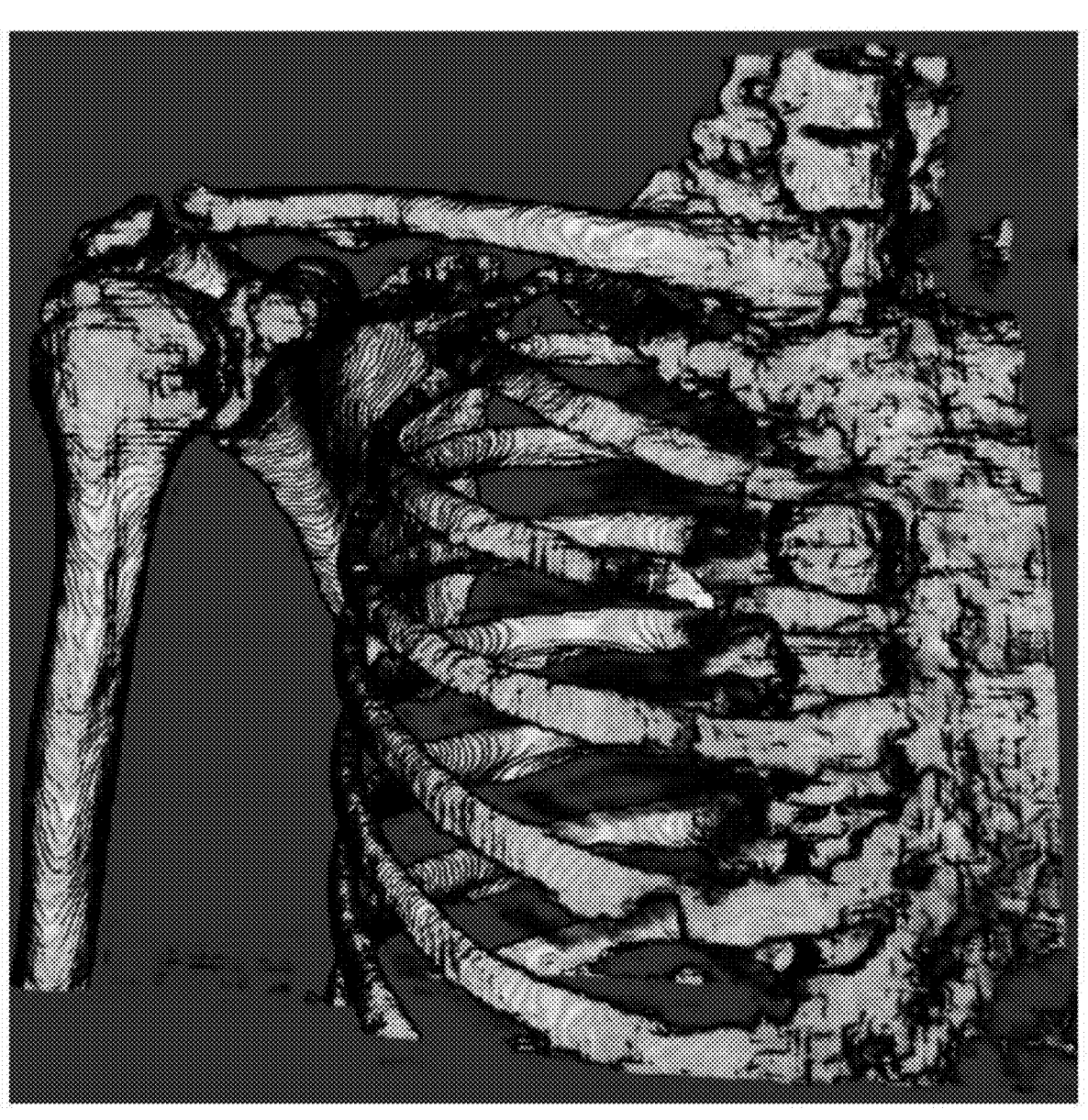
FIG. 4(c) shows a sample 3D synthesized image.
Figure 5A:
FIGS. 5(a), 6(a), and 7(a) show correct answer 3D images taken from various angles.
Figure 5B:
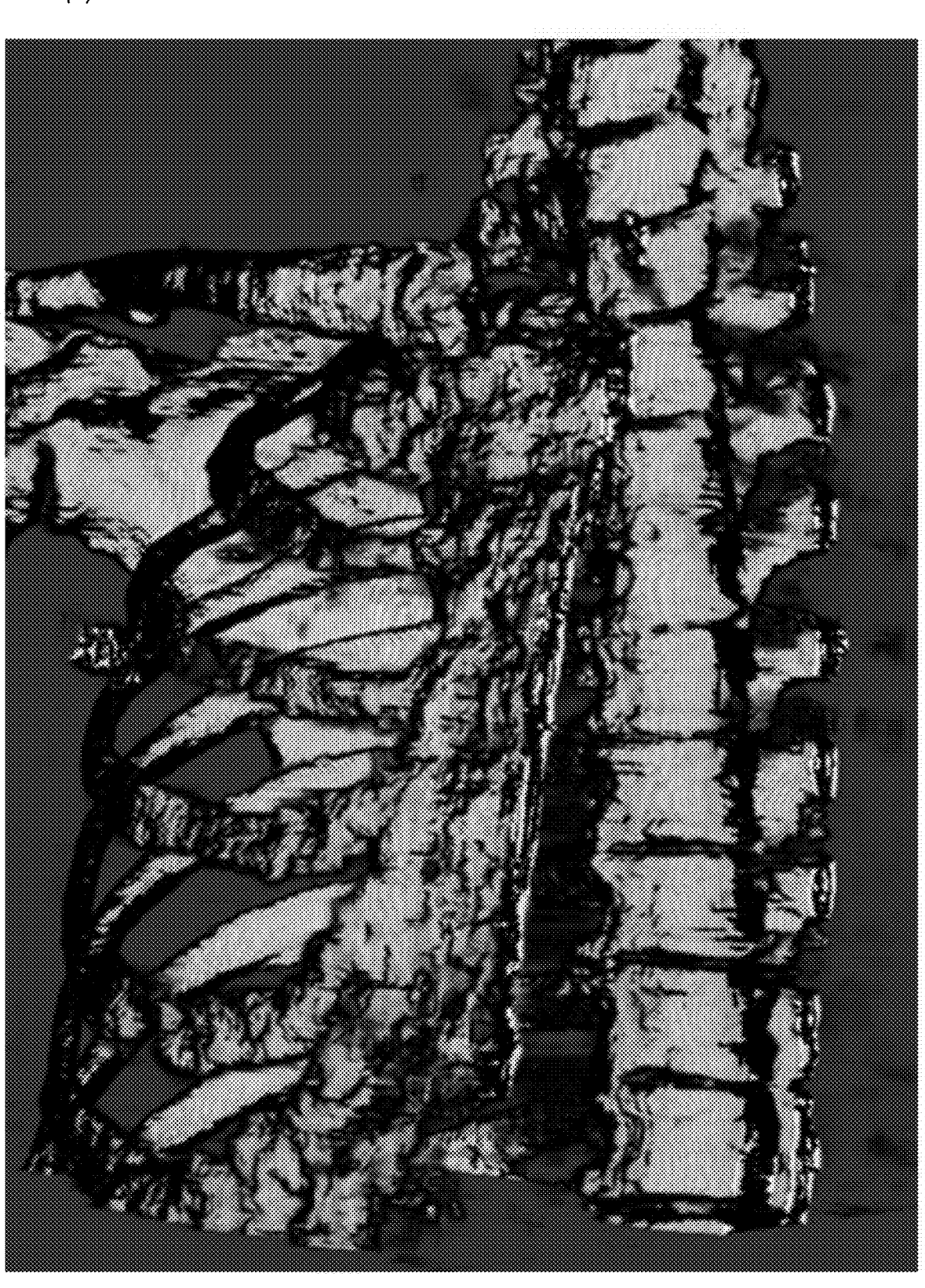
FIGS. 5(b), 6(b), and 7(b) show corresponding sample 3D synthesized images.
Figure 6A:
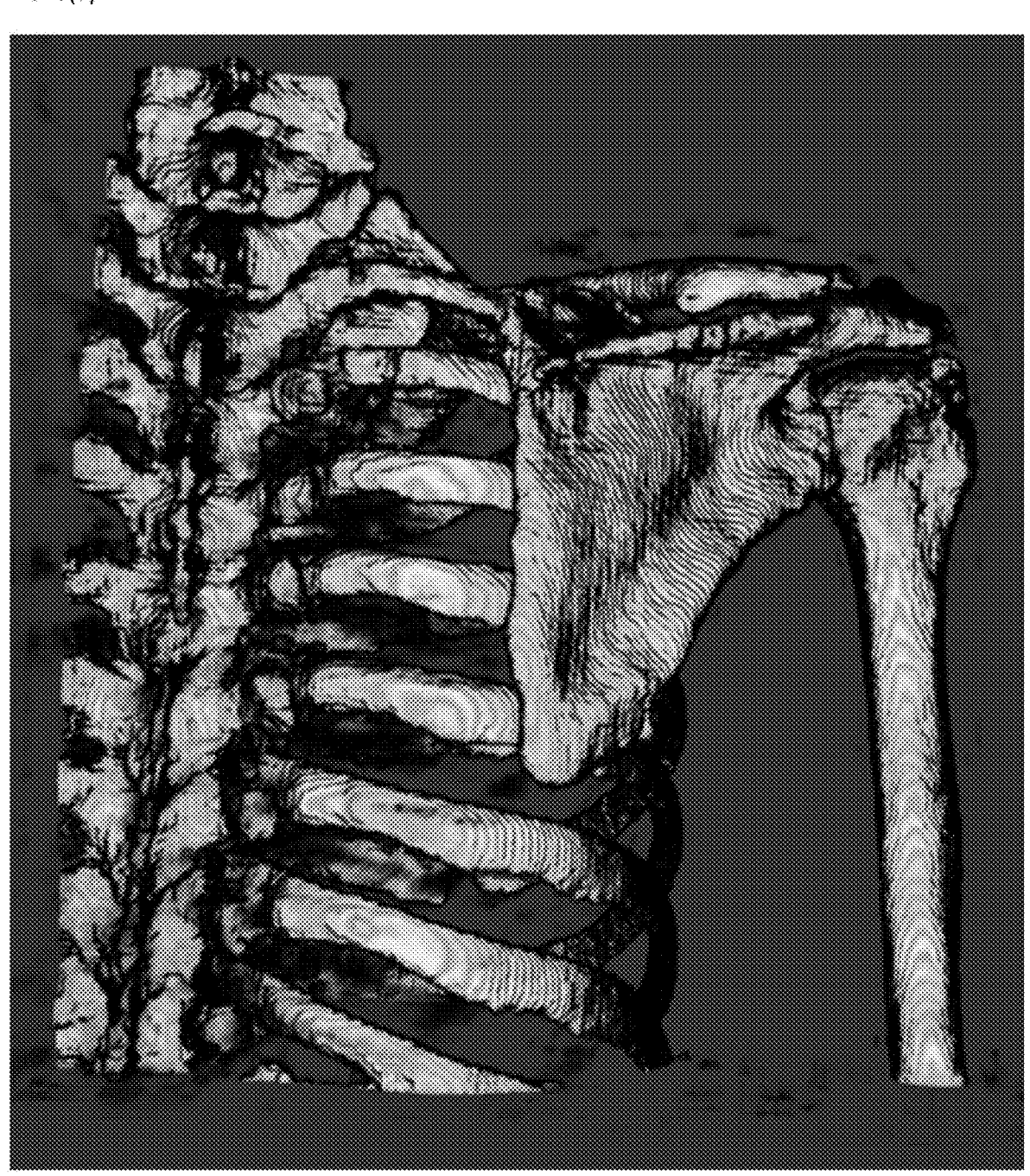
Figure 6B:
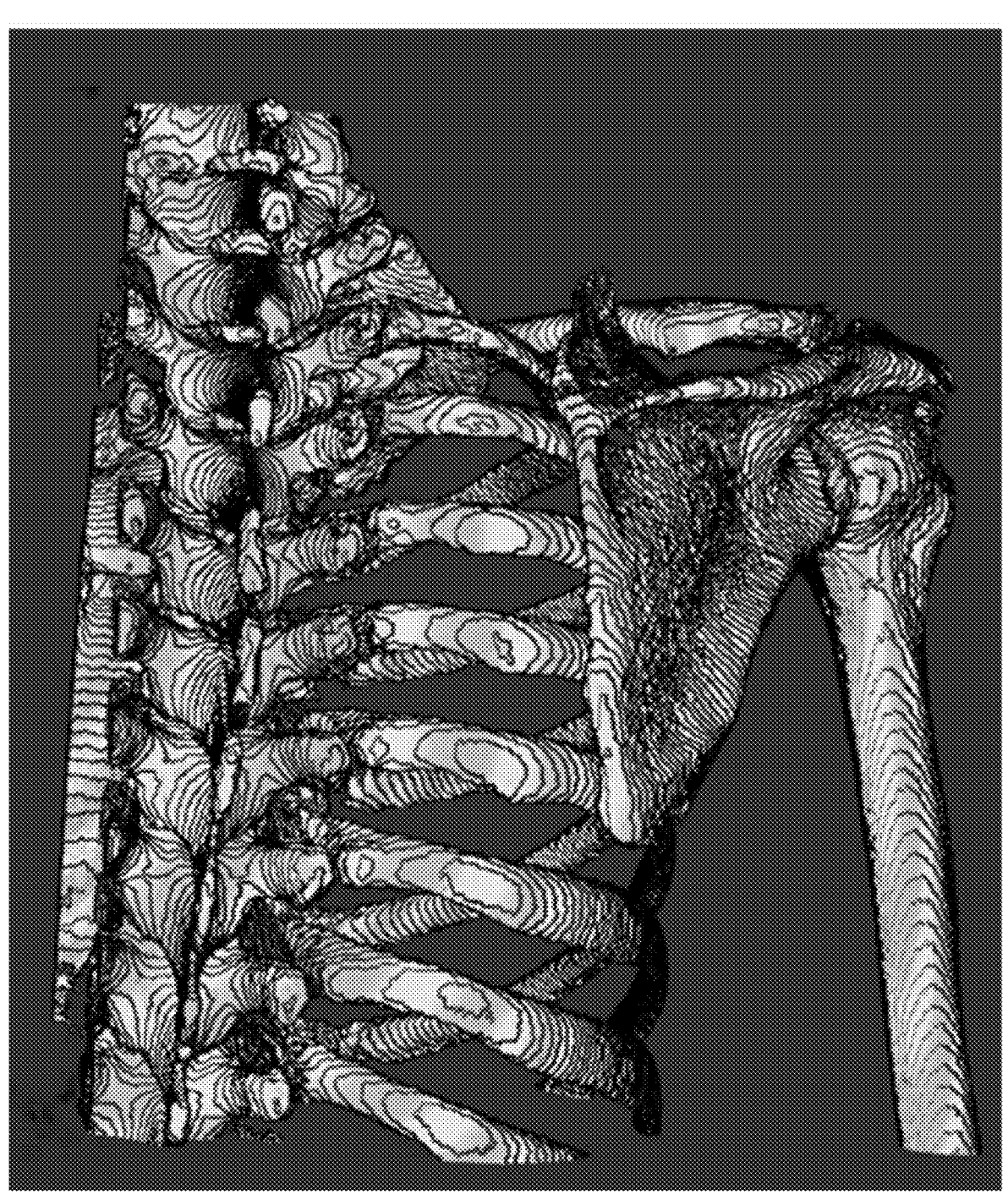
Figure 7A:
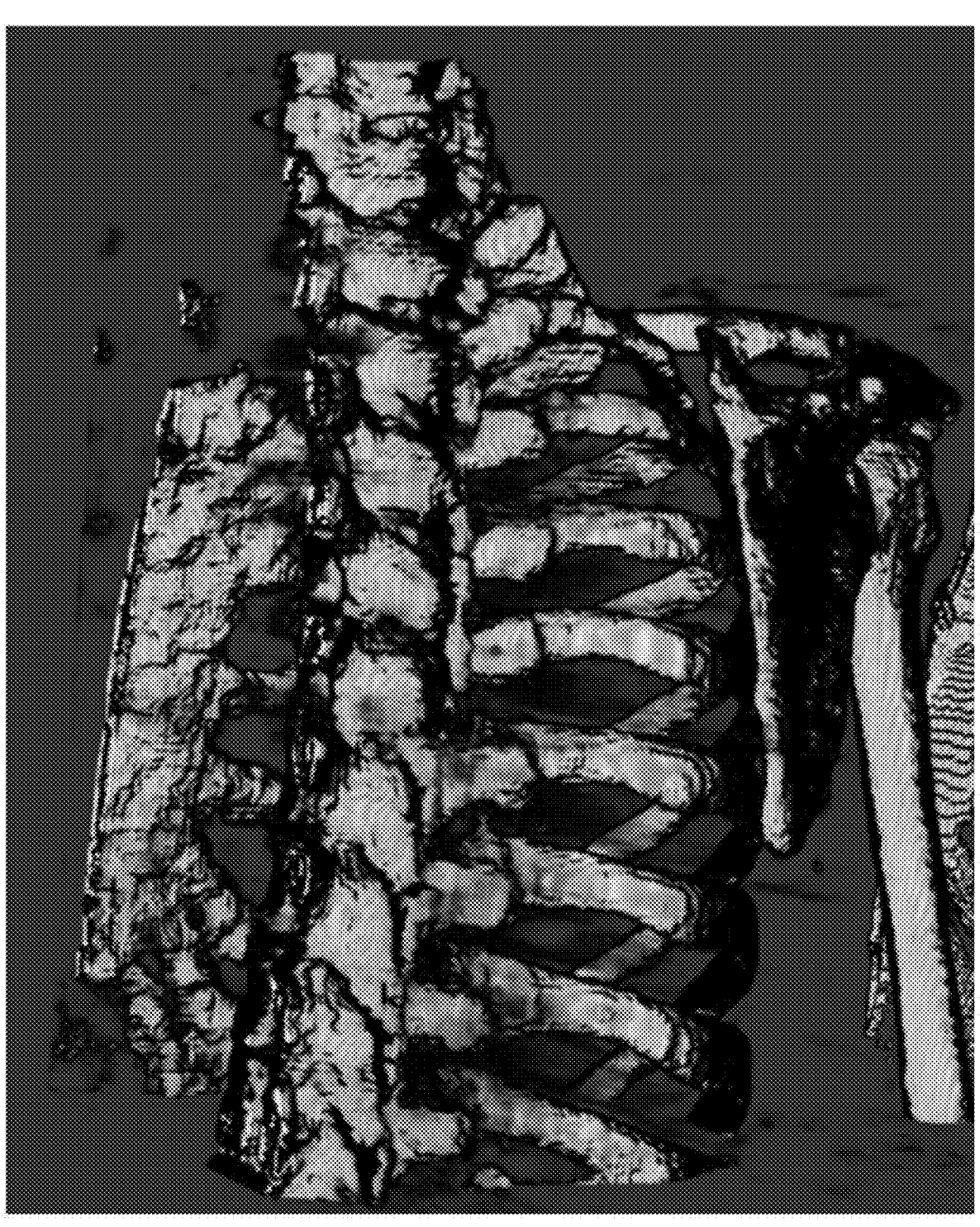
Figure 7B:
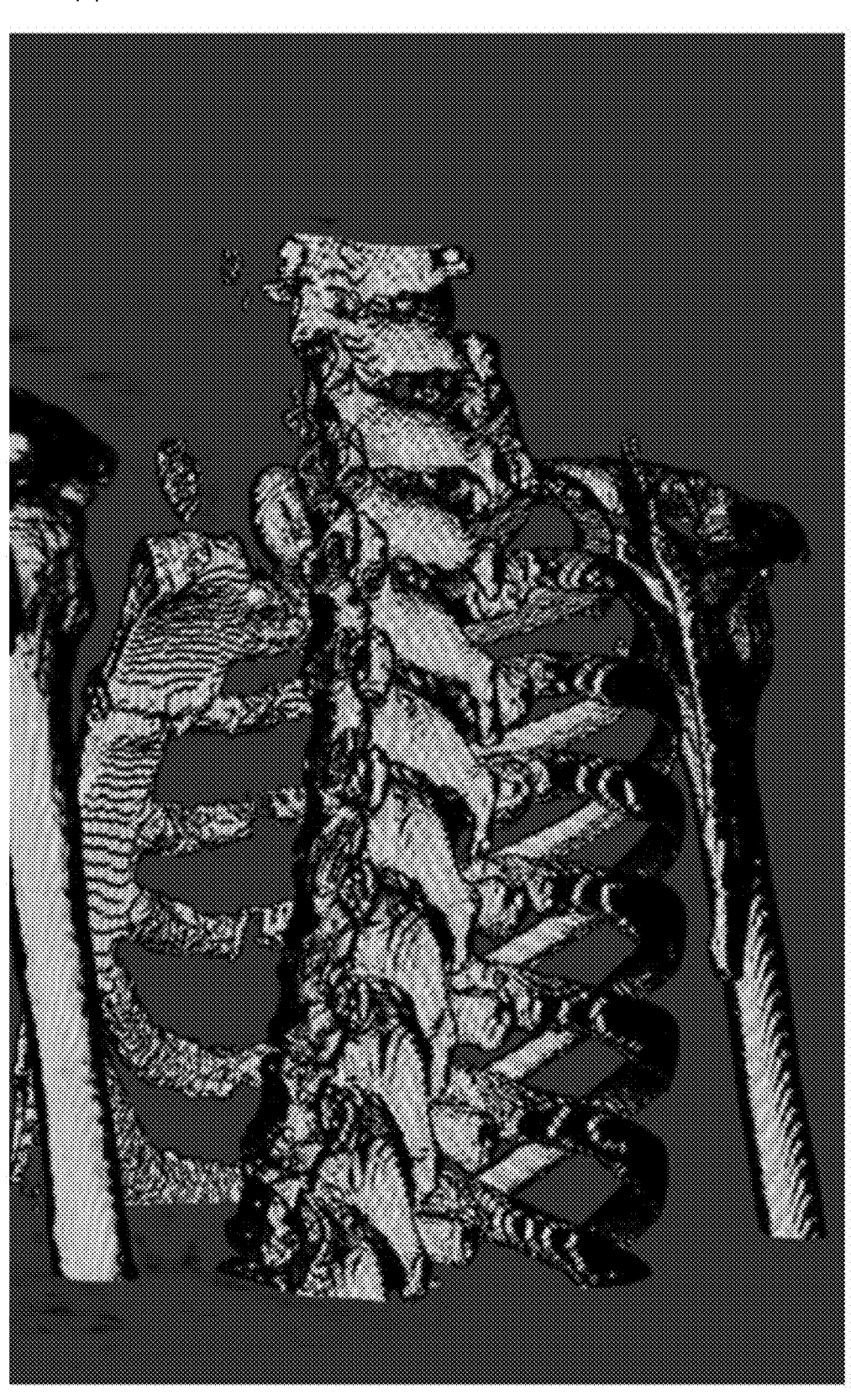

FIG. 4(a) shows the correct answer 3D image A1 in the artificial intelligence learning unit 100, FIG. 4(b) shows the sample 2D image A2, and FIG. 4(c) shows the sample 3D synthesized image A3. FIGS. 5(a), 6(a), and 7(a) show correct answer 3D images A1 taken from various angles, and FIGS. 5(b), 6(b), and 7(b) show corresponding sample 3D synthesized images A3.

In the data input unit 110 according to the present invention, a sample 3D CT image (an original image) may be input.

As an embodiment, 1,033 X-ray and CT images of 915 patients who had a CT shoulder 3D examination performed within 180 days from the date of the shoulder AP, axial, and outlet view (both) X-ray examination were collected.

In the bone segmentation and extraction unit 120 according to the present invention, the correct answer 3D image A1 in which bones may be segmented, extracted and reconstructed is generated from the input sample 3D CT image.

As a prior art, there is a method of segmenting bone areas in a CT image by setting Hounsfield ranges. In the case of this prior art, rigid areas such as bones have high Hounsfield values (e.g., 100) in a CT image, and lungs and other soft areas have low Hounsfield values in the CT image. However, when a specific organ is emphasized using a contrast agent and a contrast enhanced technique, the organ has a high Hounsfield value, making it difficult to extract only bones.

Therefore, this prior art has the problem of not being applicable to CT using a contrast agent, and also has the problem of not including the insides of bones.

The present invention proposes artificial intelligence-based bone segmentation and extraction technology to overcome the above-described problems.

The prior art corresponds to a mathematical extraction method that extracts bones by determining ranges. In contrast, a bone segmentation model according to the present invention may segment bone regions by taking into consideration anatomical locations in a CT image. Therefore, the bone segmentation model according to the present invention may be differentiated from the prior art in that it segments bone areas more precisely than the prior art and is especially applicable to CT using a contrast agent and a contrast enhanced technique. Furthermore, the precise bone segmentation according to the present invention enables more accurate 3D image reconstruction in subsequent steps.

As an embodiment, a bone segmentation model based on artificial intelligence called TransUnet may be developed and segment bone areas in a CT image.

The bone segmentation and extraction unit 120 according to the present invention may perform operation by using a deep learning segmentation technique.

It may be appropriate that the deep learning segmentation technique be any one of image segmentation and semantic segmentation. Furthermore, various other segmentation techniques are applicable to the present invention.

The image segmentation refers to segmenting a digital image into individual groups of pixels for object detection and semantic classification. Among the image segmentation techniques, semantic segmentation is the process of dividing a digital image into multiple sets of pixels. Semantic segmentation means converting the representation of an image into something that is easier to interpret by simplifying it through segmentation.

Figure 8:
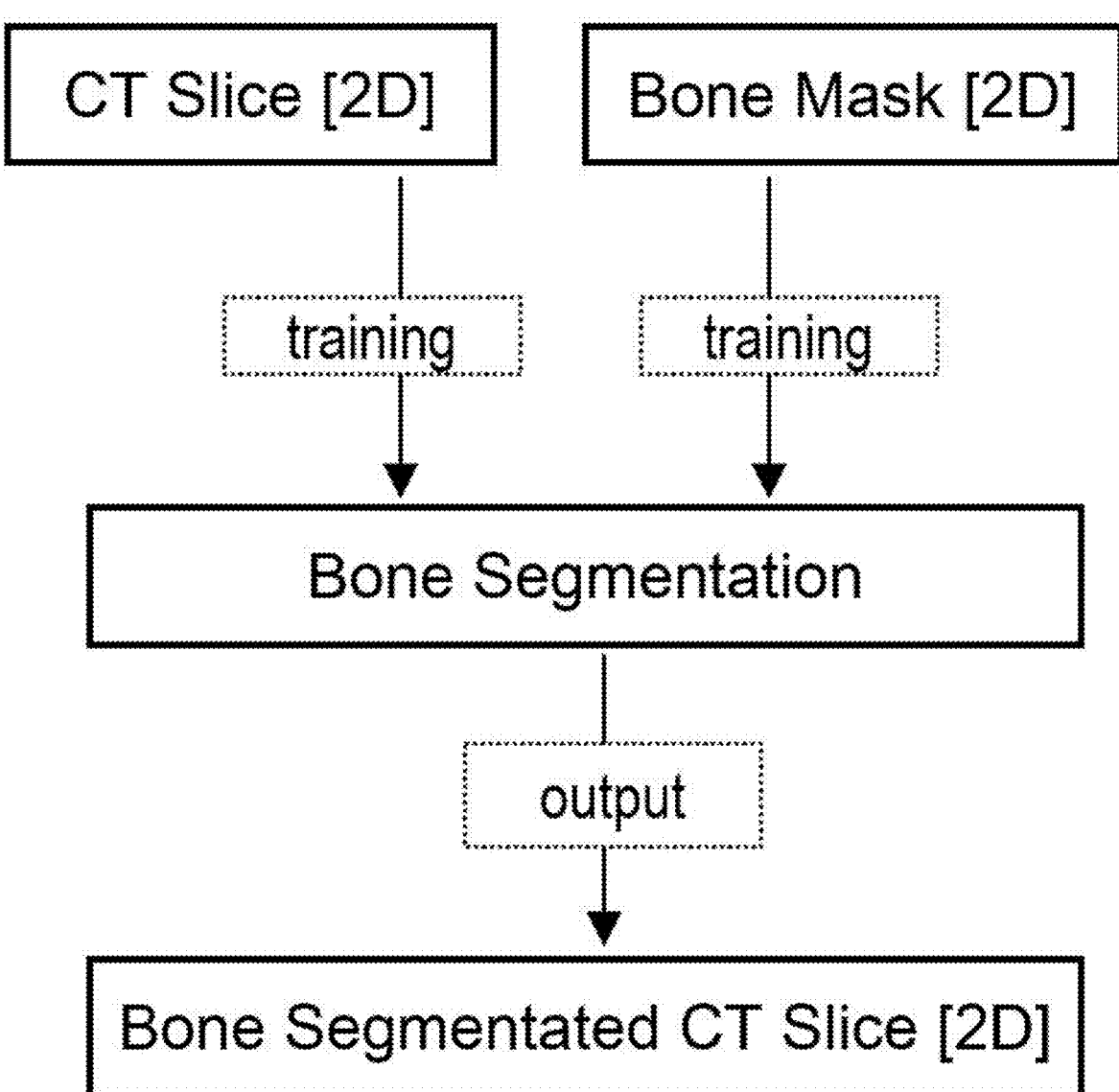
FIG. 8 is a flowchart of the training of a bone extraction model showing the operating principle of a bone segmentation and extraction unit, which shows the process and results of training an artificial intelligence segmentation model to extract (segment) only bone regions from a CT image.

FIG. 8 is a flowchart of the training of a bone extraction model showing the operating principle of the bone segmentation and extraction unit 120. This drawing shows the process and results of training an artificial intelligence segmentation model to extract (segment) only bone regions from a CT image.

The bone segmentation technique performed in the bone segmentation and extraction unit 120 according to the present invention will be described based on the individual steps thereof in more detail as follows.

In a first step, individual slices of CT images are input to a bone segmentation model as training data.

In a second step, training data in which bone regions for the slices are masked is input to the bone segmentation model.

In a third step, the bone segmentation model is trained to specify the bone regions for the individual slices of the CT images input in the first and second steps.

In a fourth step, the locations of bones are predicted by inputting individual slices of a CT image to the trained bone segmentation model.

FIG. 6 is a photograph showing bones (in brown) segmented in a CT area by using a bone segmentation model. FIG. 6 visualizes a situation in which only bone regions marked in brown are extracted from each CT image. From this drawing, it can be seen that bone regions such as the clavicle, the scapula, and the humerus were well extracted from various anatomical structures.

Figure 9A:
FIGS. 9 to 11 are photographic data showing bones (in brown) segmented in a CT area by using a bone segmentation model.
Figure 9B:
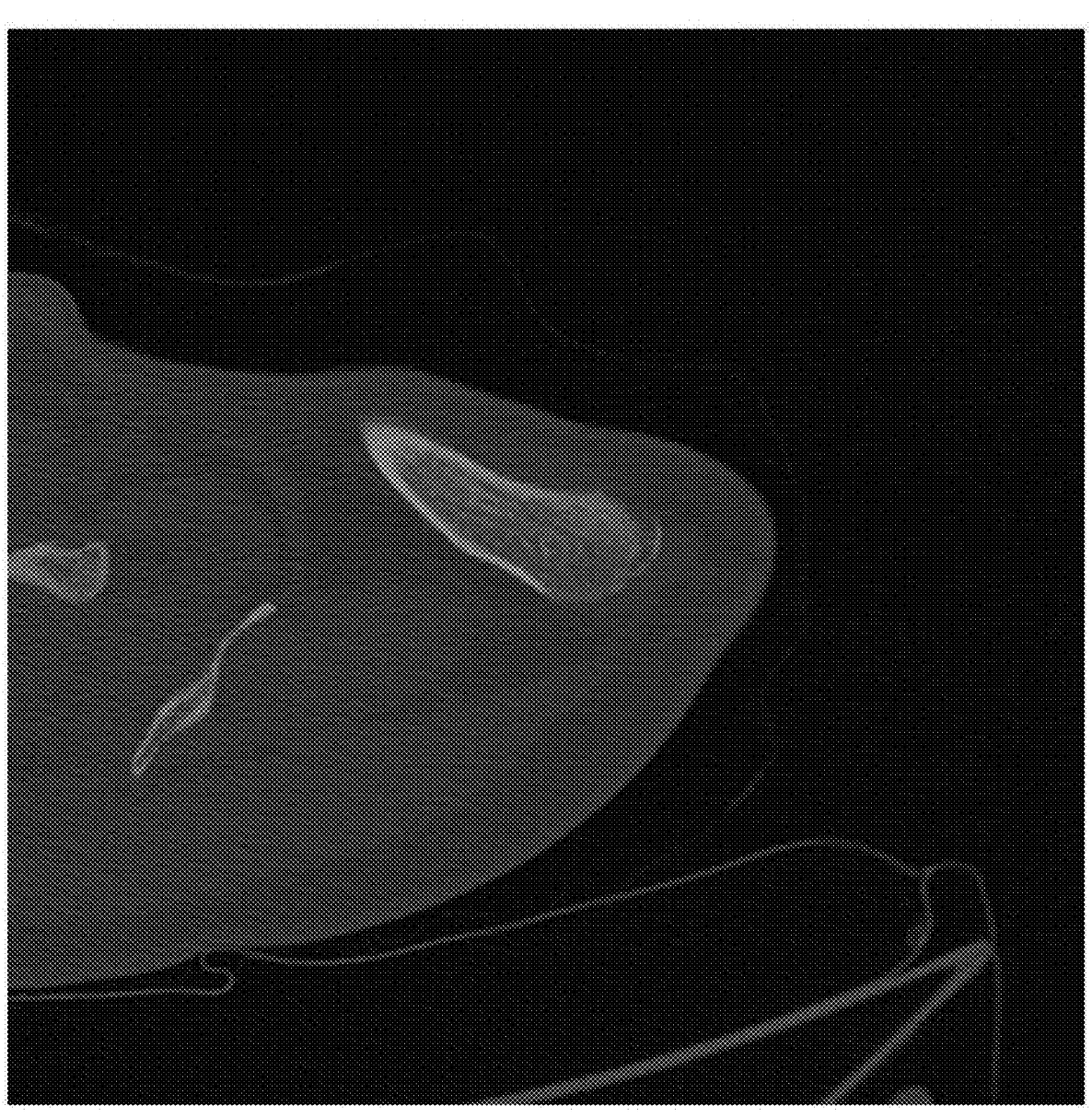
Figure 10A:
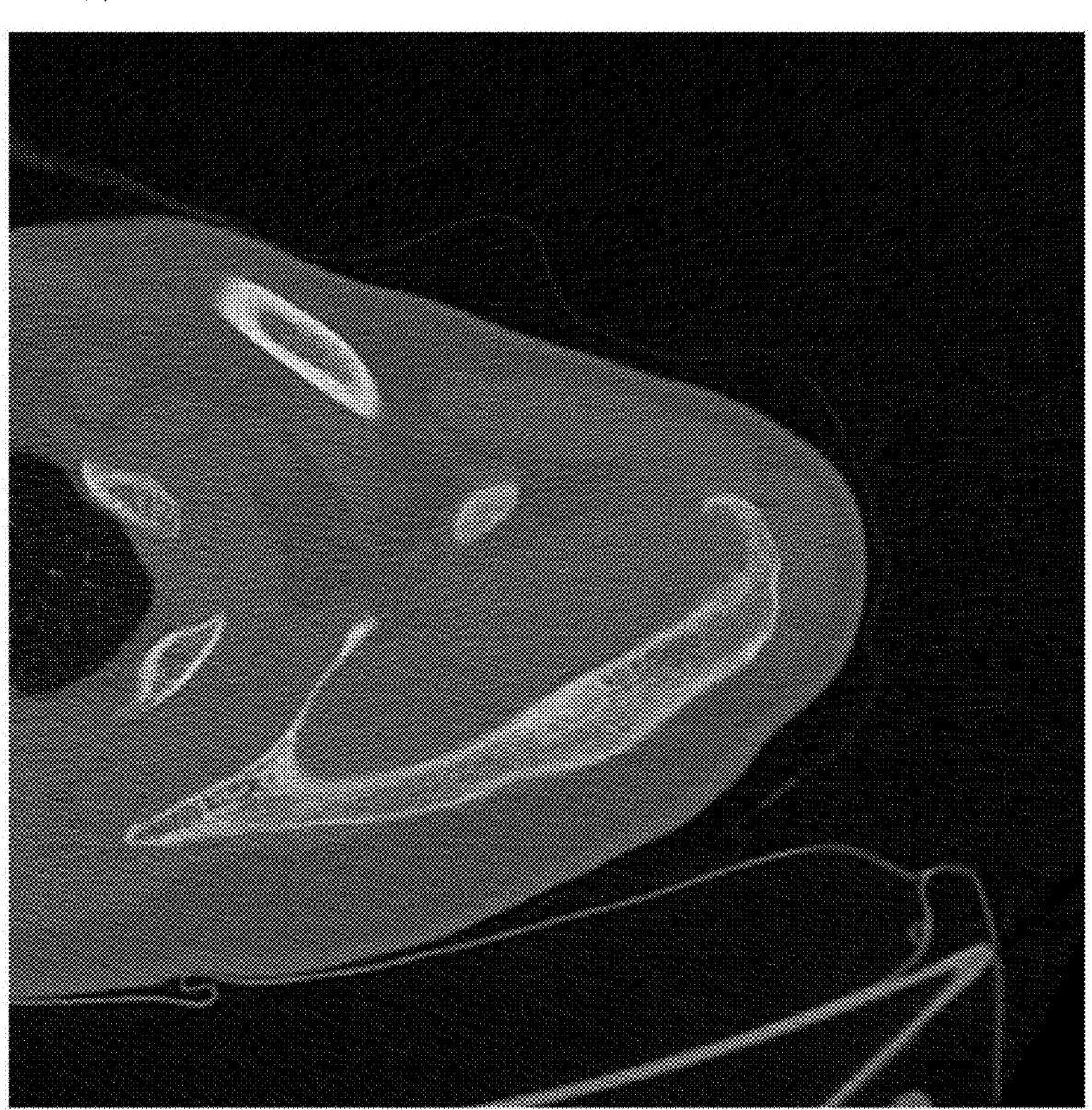
Figure 10B:
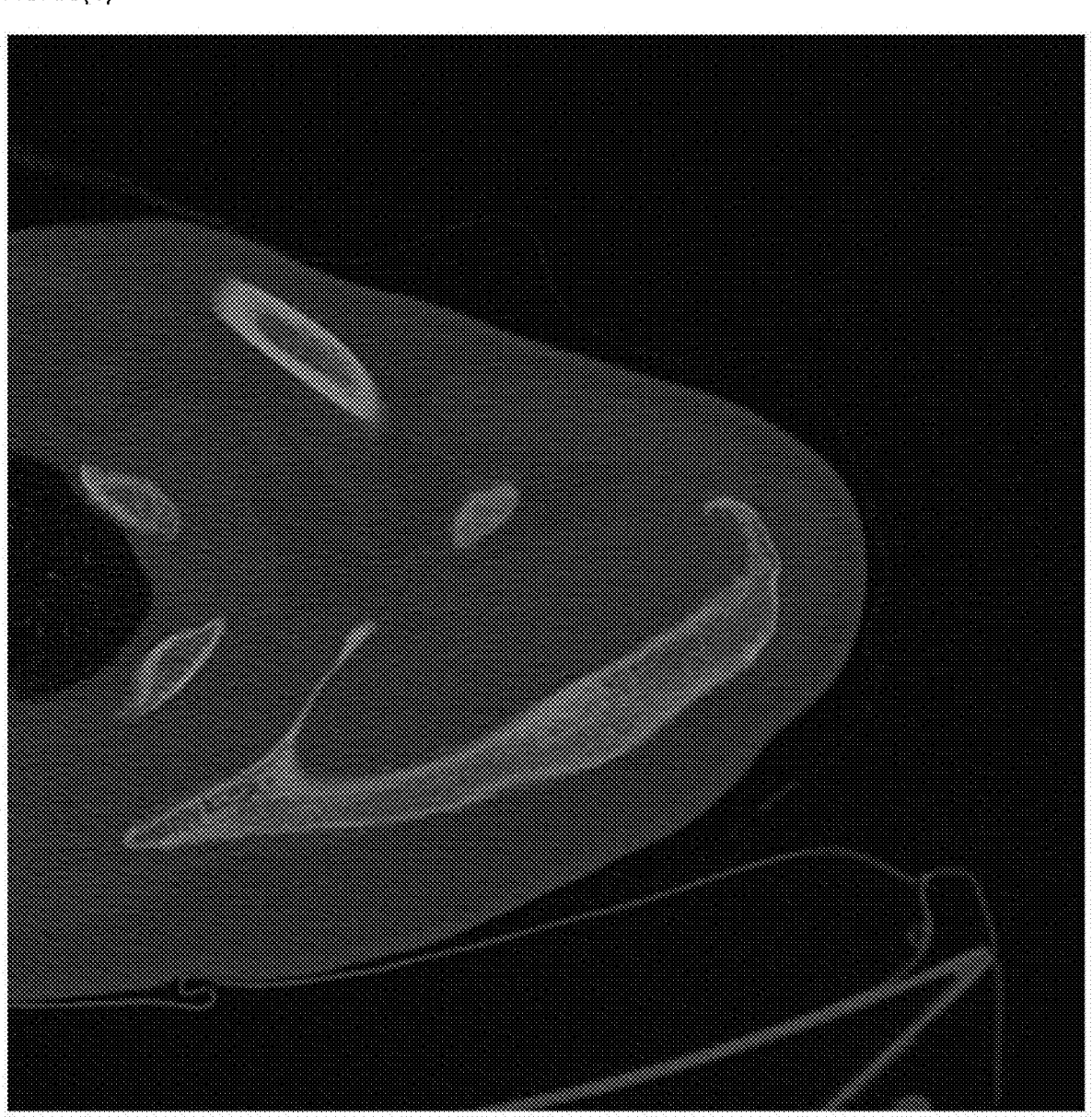
Figure 11A:
Figure 11B:

FIGS. 9 to 11 are photographic data showing bones (in brown) segmented in a CT area by using a bone segmentation model. FIGS. 9(a), 10(a), and 11(a) show original CT slices, and FIGS. 9(b), 10(b), and 11(b) visualize the segmented bones (brown) inferred from the original CT slices by the bone segmentation model. From these drawings, it can be seen that bone regions such as the clavicle, the scapula, and the humerus were well extracted from various anatomical structures.

In the sample 2D image generation unit 130 according to the present invention, the sample 2D image A2 may be generated from the correct answer 3D image A1 generated by the bone segmentation and extraction unit 120.

The sample 2D image generation unit 130 may perform operation by using an MIP technique. Through this, data similar to X-ray data may be generated.

In this case, the MIP technique refers to a technique that allows only the part having the maximum shading intensity among the tissues overlapping at one point to appear in an image when a predetermined area is generated in the form of an image of one cross section.

FIG. 4(a) shows the correct answer 3D image A1 obtained by segmenting and extracting bones from the sample 3D CT image, and FIG. 4(b) shows the sample 2D image A2 obtained by performing MIP conversion on the image of FIG. 12(a). To overcome the problem in which training is not easily performed because the exact alignment between an X-ray image and a CT image is not achieved, the present invention has the technical feature of generating an MIP image as shown in FIG. 4(b).

In the learning model construction unit 140 according to the present invention, the sample 3D synthesized image A3 may be generated from the sample 2D image A2 generated by the sample 2D image generation unit 130 (see FIG. 4) Furthermore, an artificial intelligence learning model may be constructed as the generated sample 3D synthesized image A3 is learned by being compared with the correct answer 3D image A1.

The learning model construction unit 140 may perform operation by using a Generative Adversarial Network (GAN) technique.

In this case, the GAN (Generative Adversarial Network) refers to a model (Network) in which a generator and a discriminator compete with each other (Adversarial) to generate data (Generative).

In the present invention, the generator generates the sample 3D synthesized image A3, and the discriminator evaluates the generated sample 3D synthesized image A3. The main operating principle is that training progresses in such a manner that the generator and the discriminator compete with each other and gradually improve each other's performance.

More specifically, a technical configuration using a GAN is described in more detail based on the individual steps thereof as follows.

In a first step, a sample 2D image A2, which is an MIP image, is input to a generator.

In a second step, a correct answer 3D image A1 in which bones have been segmented is input to a discriminator.

In a third step, the generator is trained to generate a sample 3D synthesized image A3, which is a synthesized bone segmented CT image, by using the sample 2D image A2.

In a fourth step, the discriminator compares the sample 3D synthesized image A3, synthesized by the generator, with the correct answer 3D image A1 corresponding to actual ground truth.

In a fifth step, the generator generates a sample 3D synthesized image A3, which is a more elaborately synthesized bone segmented CT image, while the third and fourth steps are repeated.

Figure 13A:
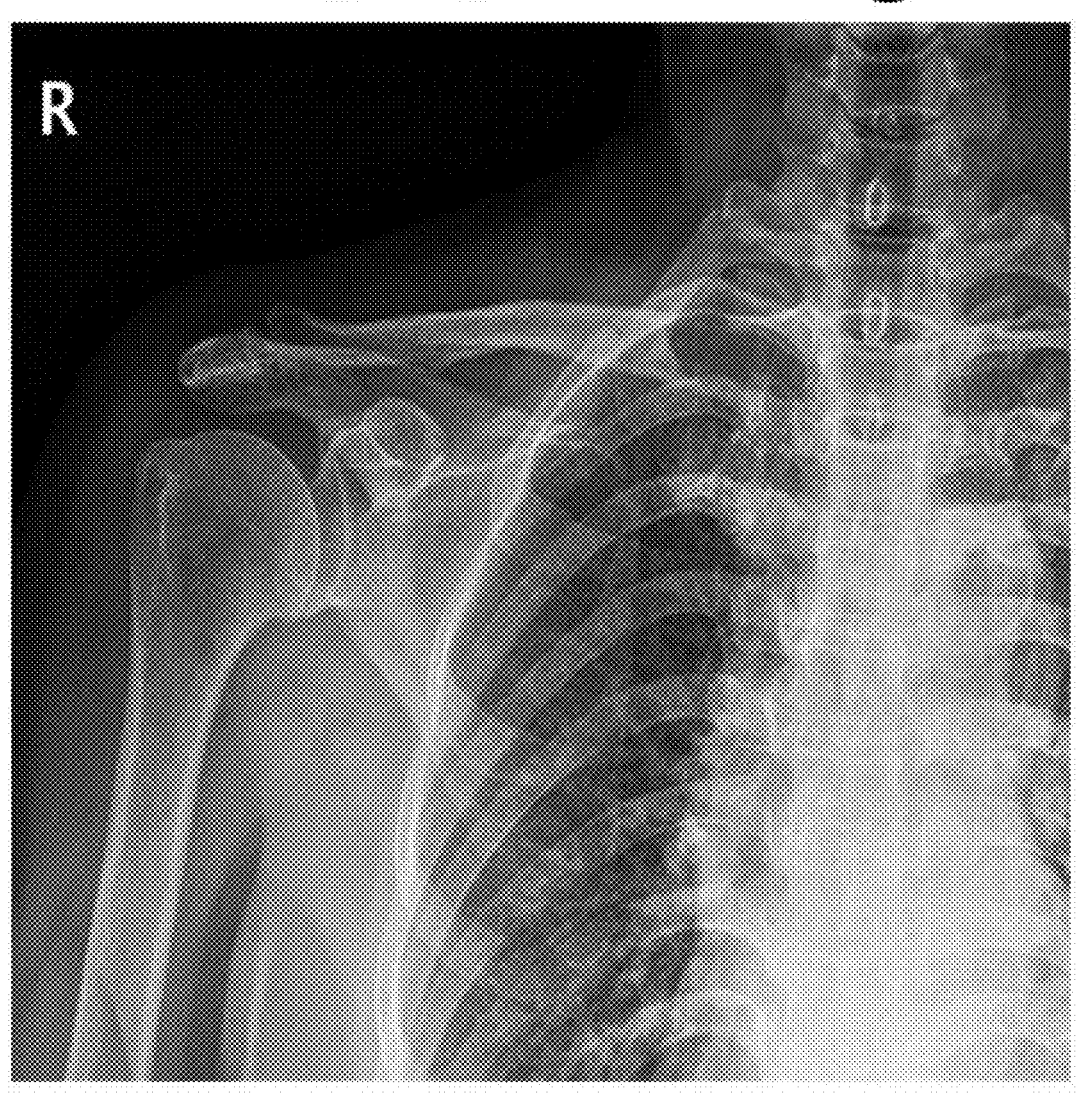
FIG. 13(a) shows a target 2D X-ray image, which is an original image, in the MIP image conversion unit.
Figure 13B:
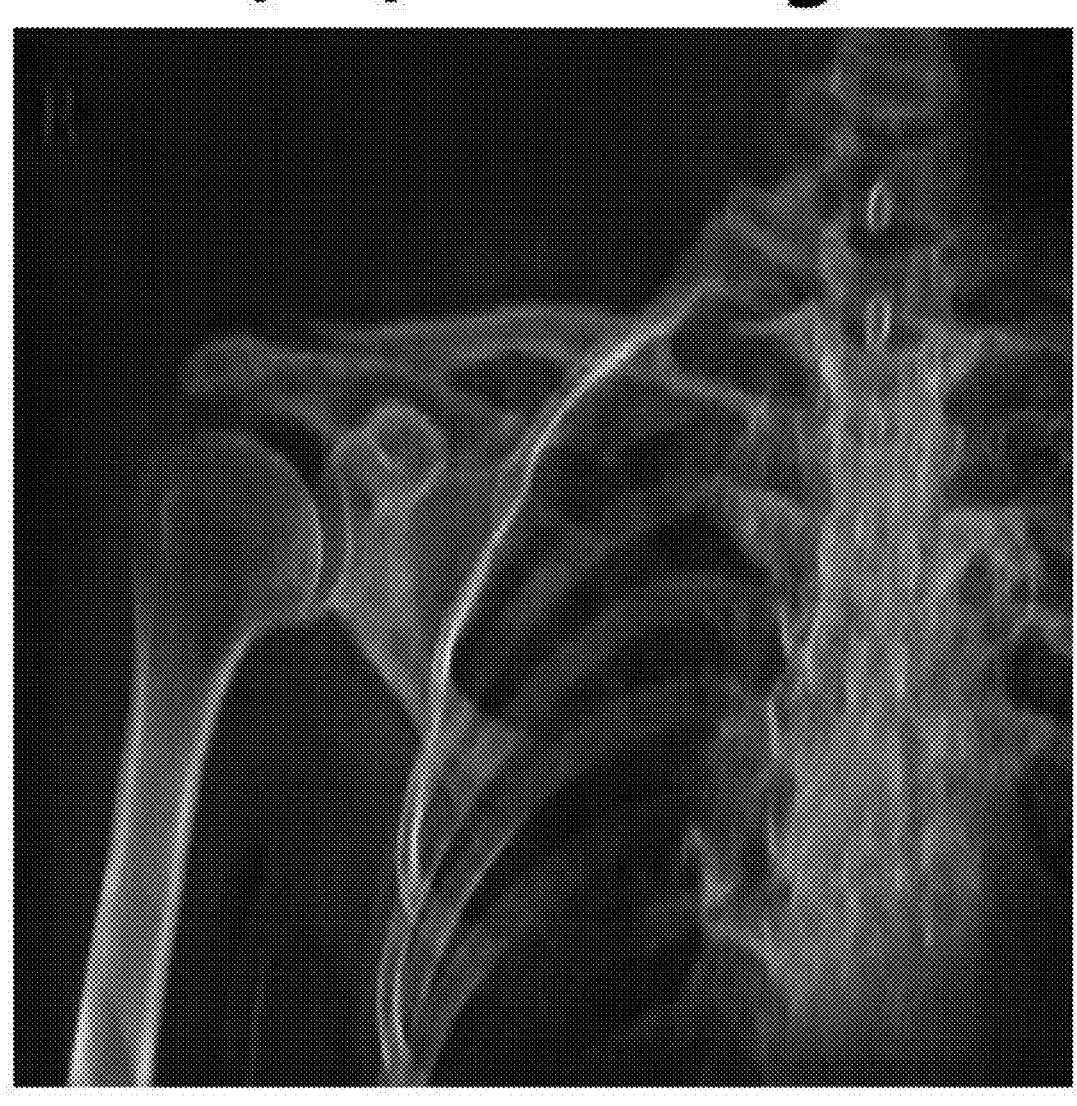
FIG. 13(b) shows a target 2D MIP image converted into an MIP image by a Cycle GAN model.

In a sixth step, a synthesized bone segmented CT image is generated by inputting an MIP image to the trained generator. The image generated by the trained model is shown in FIG. 13.

In addition, the correct answer 3D image A1 is shown in FIG. 4(*a*), and the 2D image A2 is obtained by subjecting the 3D image A1 to MIP conversion. The obtained 2D image A2 is learned by being compared with the correct answer 3D image A1 in the learning model. As a result of the comparative learning, the 3D image A3 is generated. For example, the 3D image A3 is generated multiple times (see A3-1, A3-2, A3-3, etc.), and finally, the sample 3D synthesized image A3, which is a final image having a preset similarity level with the correct answer 3D image A1, may be generated.

The MIP image conversion unit 200 according to the present invention will be described below.

In the MIP image conversion unit 200 according to the present invention, the input target 2D X-ray image B1 and the sample 2D image A2 may be input to a preset learning model, and thus, the target 2D MIP image B2 may be generated.

The MIP image conversion unit 200 may include: a data input unit 210 configured such that the target 2D X-ray image B1 and the sample 2D image A2 are input thereto; and an MIP learning unit 220 configured such that the target 2D X-ray image B1 and sample 2D image A2 input to the data input unit 210 are input to the learning model, and thus, the target 2D MIP image B2 is generated.

In the MIP learning unit 220 according to the present invention, the input target 2D X-ray image B1 may be generated as the target 2D MIP image B2 by an MIP technique.

In the MIP learning unit 220 according to the present invention, the training may be performed using a Cycle GAN model.

The operating principle of a process of converting an X-ray image into an MIP image in the MIP image conversion unit 200 will be described based on the individual steps thereof in more detail as follows.

In a first step, an input target 2D X-ray image B1 and a sample 2D image A2 are input to the Cycle GAN model.

In a second step, the cycle GAN model is trained to convert the target 2D X-ray image B1 into the sample 2D image A2.

In a third step, the trained Cycle GAN model converts the 2D X-ray image B1 into an MIP image B2.

Figure 12:
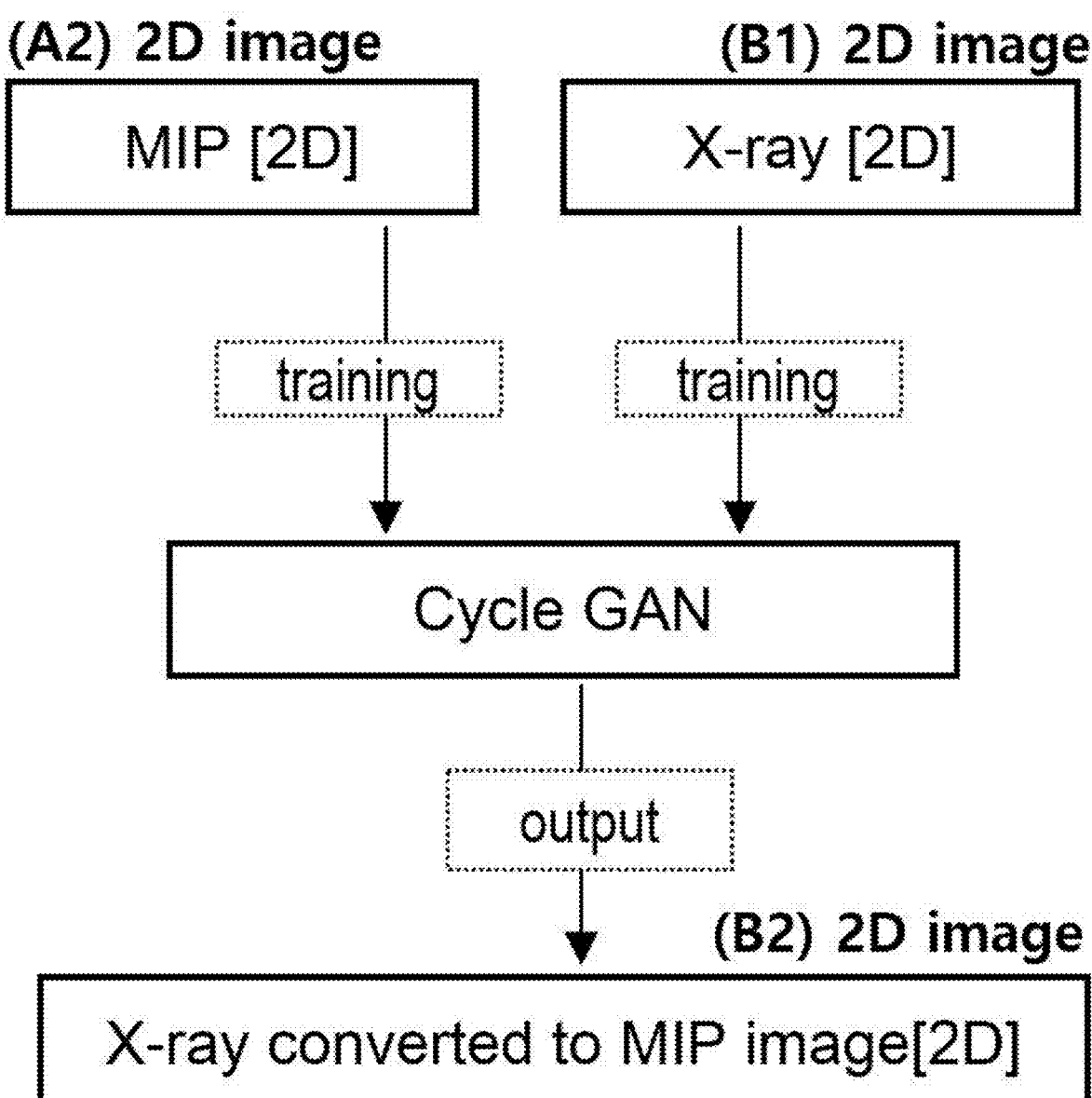
FIG. 12 is a flowchart of a process of converting an X-ray image into an MIP image by using a Cycle GAN model in an MIP image conversion unit.

FIG. 12 is a flowchart of a process of converting an X-ray image into an MIP image by using a Cycle GAN model in the MIP image conversion unit 200. Since the model that generates a 3D CT image is trained using MIP images, a process of converting an X-ray image into an MIP image is required. This drawing shows a process of the training and operation results of the Cycle GAN model.

FIG. 13(*a*) shows the target 2D X-ray image B1, which is an original image, in the MIP image conversion unit 200, and FIG. 13(*b*) shows the target 2D MIP image B2 converted into an MIP image by the Cycle GAN model.

The final 3D synthesized image output unit 300 according to the present invention will be described below.

In the final 3D synthesized image output unit 300 according to the present invention, the target 2D MIP image B2 converted by the MIP image conversion unit 200 may be input to the learning model constructed by the artificial intelligence learning unit 100, and thus, a final 3D synthesized image C1 may be output.

Figure 14:
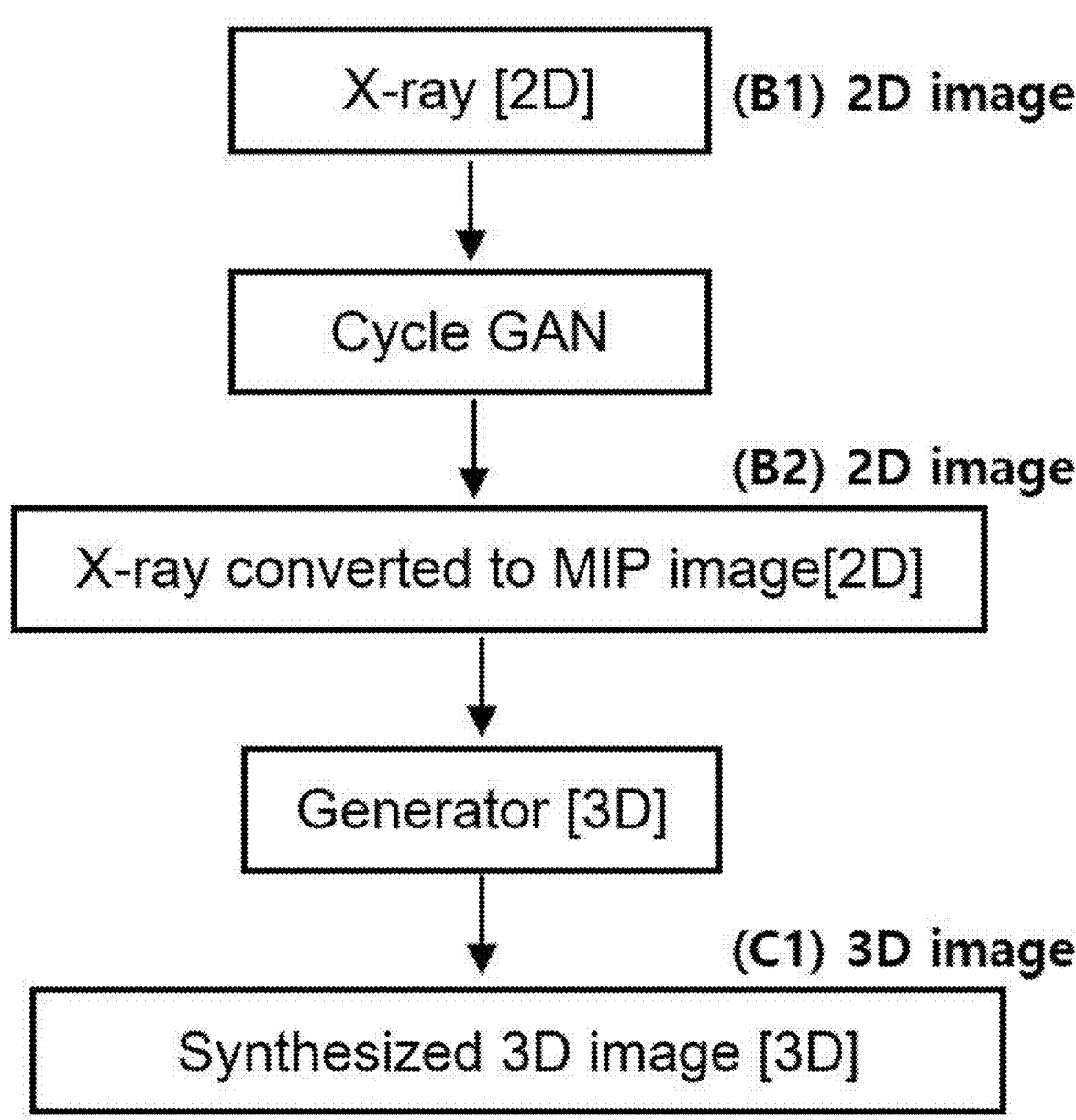
FIG. 14 shows the operating principle of a final 3D synthesized image output unit and shows a flowchart of a process in which an artificial intelligence model finally generates a synthesized CT image.

FIG. 14 shows the operating principle of the final 3D synthesized image output unit 300 and also shows a flowchart of a process in which the artificial intelligence model finally generates a synthesized CT image.

This drawing shows a process of generating a final 3D synthesized image C1 of a patient by using a generator trained by comparing an MIP image with an original sample 3D CT image of a third party after converting a target 2D X-ray image B1 of the patient into an MIP image B2.

The operating principle of the final 3D synthesized image output unit 300 will be described based on the individual steps thereof in more detail as follows.

In a first step, a target 2D MIP image B2 converted into an MIP image is input to the generator of the learning model that is constructed in the artificial intelligence learning unit 100.

In a second step, the generator outputs a final 3D synthesized image C1.

Meanwhile, the present invention may be implemented as an image reconstruction method invention. More specifically, the present invention may be implemented as an image reconstruction method of outputting a 3D synthesized image from a 2D X-ray image based on artificial intelligence.

Although this method invention is different in invention category from the above-described system invention, the technical configuration thereof is substantially the same as that of the system invention. Accordingly, descriptions of the technical configurations of the method invention that are the same as those of the system invention will be replaced with the above descriptions, and the following description will focus on the gist of the present method invention.

The present invention provides an image reconstruction method that is performed by a control server having a database and a computation function and outputs a 3D synthesized image from a 2D X-ray image based on artificial intelligence, the image reconstruction method including: step S100 configured such that in the artificial intelligence learning unit 100, a correct answer 3D image A1 in which bones are segmented and extracted is generated from a sample 3D CT image, a sample 2D image A2 is generated from the correct answer 3D image A1, a sample 3D synthesized image A3 is generated from the 2D image A2, and an artificial intelligence learning model is constructed as the generated sample 3D synthesized image A1 is learned by being compared with the correct answer 3D image A1; step S200 configured such that in the MIP image conversion unit 200, an input target 2D X-ray image B1 and the sample 2D image A2 are input to a preset learning model, and thus, a target 2D MIP image B2 is generated; and step S300 configured such that in the final 3D synthesized image output unit 300, the target 2D MIP image B2 generated in the MIP image conversion unit 200 is input to the learning model constructed in the artificial intelligence learning unit 100, and thus, a final 3D synthesized image C1 is output.

In step S100, there are performed step S110 configured such that in the data input unit 110, the sample 3D CT image is input thereto; step S120 configured such that in the bone segmentation and extraction unit 120, the correct answer 3D image A1 in which bones are segmented, extracted and reconstructed is generated from the input sample 3D CT image; step S130 configured such that in the sample 2D image generation unit 130, the sample 2D image A2 is generated from the correct answer 3D image A1 generated in the bone segmentation and extraction unit 120; and step S120 configured such that in the learning model construction unit 140, the sample 3D synthesized image A3 is generated from the sample 2D image A2 generated in the sample 2D image generation unit 130 and the artificial intelligence learning model is constructed as the generated sample 3D synthesized image A3 is learned by being compared with the correct answer 3D image A1.

Step S130 may be performed using an MIP technique.

In step S140, the training may be performed using a GAN model.

In step S200, there are performed step S210 configured such that in the data input unit 210, the target 2D X-ray image B1 and the sample 2D image A2 are input thereto, and step S210 configured such that in the MIP learning unit 220, the target 2D X-ray image and sample 2D image input to the data input unit 210 are input to the learning model, and thus, the target 2D MIP image B2 is generated.

In step S220, the input target 2D X-ray image B1 may be generated as the target 2D MIP image B2 by an MIP technique.

In step S220, the training may be performed using a Cycle GAN model.

Furthermore, the present invention may be implemented as a computer program. More specifically, the present invention may be implemented as a computer program that is combined with hardware and stored in a computer-readable storage medium in order to enable an image reconstruction method of outputting a 3D synthesized image from a 2D X-ray image based on artificial intelligence according to the present invention to be executed by a computer.

The methods according to embodiments of the present invention may be implemented in the form of programs readable through various computer means, and may be recorded on a computer-readable storage medium. In this case, the storage medium may include program instructions, data files, data structures, etc. alone or in combination thereof. The program instructions stored on the storage medium may be those specifically designed and constructed for the present invention, or may be known and available to those having ordinary skill in the art to which computer software pertains. For example, the storage medium includes magnetic media such as a hard disk, a floppy disk and magnetic tape, optical media such as CDROM and DVD, magneto-optical media such as a floptical disk, and hardware devices specifically configured to store and execute program instructions such as ROM, RAM, flash memory, etc. Examples of the program instructions may include a machine language such as that generated by a compiler, as well as a high-level language that can be executed by a computer using an interpreter or the like. These hardware devices may each be configured to operate as one or more software modules to perform the operation of the present invention, and vice versa.

The image reconstruction system and method for outputting a 3D synthesized image from a 2D X-ray image based on artificial intelligence according to the present invention have the following advantages:

A first advantage is to, based on artificial intelligence, synthesize a reconstructed 3D stereoscopic image of CT of bones by using one or more 2D plane radiographs (e.g., X-ray images).

A second advantage is to increase the quality of a synthesized 3D stereoscopic image by using a GAN or Cycle GAN learning model.

A third advantage is to overcome the problem, in which training is not easily performed because the exact alignment between an X-ray image and a CT image is not achieved, by converting an X-ray image into an MIP image.

The advantages of the present invention are not limited to those mentioned above, and other advantages not mentioned will be clearly understood by those having ordinary skill in the art from the foregoing description.

The embodiments described herein and the accompanying drawings merely illustrate some of the technical spirit included in the present invention. Accordingly, the embodiments disclosed herein are not intended to limit the technical spirit of the present invention but are intended to illustrate it, so that it is obvious that the scope of the technical spirit of the present invention is not limited to these embodiments. It should be appreciated that all the modifications and specific embodiments that can be easily inferred within the technical spirit included in the specification and drawings of the present application are included in the scope of the rights of the present invention.

What is claimed is:

1. An image reconstruction system that is operated by a control server having a database and a computation function and outputs a three-dimensional (3D) synthesized image from a two-dimensional (2D) X-ray image based on artificial intelligence, the image reconstruction system comprising:

an artificial intelligence learning unit configured such that a correct answer 3D image in which bones are segmented and extracted is generated from a sample 3D computed tomography (CT) image, a sample 2D image is generated from the correct answer 3D image, a sample 3D synthesized image is generated from the 2D image, and an artificial intelligence learning model is constructed as the generated sample 3D synthesized image is learned by being compared with the correct answer 3D image;

a Maximum Intensity Projection (MIP) image conversion unit configured such that an input target 2D X-ray image and the sample 2D image are input to a preset learning model, and thus, a target 2D MIP image is generated; and a final 3D synthesized image output unit configured such that the target 2D MIP image generated in the MIP image conversion unit is input to the learning model constructed in the artificial intelligence learning unit, and thus, a final 3D synthesized image is output.

2. The image reconstruction system of claim 1, wherein the artificial intelligence learning unit comprises:

a data input unit configured such that the sample 3D CT image is input thereto;

a bone segmentation and extraction unit configured such that the correct answer 3D image in which bones are segmented, extracted and reconstructed is generated from the input sample 3D CT image;

a sample 2D image generation unit configured such that the sample 2D image is generated from the correct answer 3D image generated in the bone segmentation and extraction unit; and a learning model construction unit configured such that the sample 3D synthesized image is generated from the sample 2D image generated in the sample 2D image generation unit and the artificial intelligence learning model is constructed as the generated sample 3D synthesized image is learned by being compared with the correct answer 3D image.

3. The image reconstruction system of claim 2, wherein the bone segmentation and extraction unit performs operation by using a deep learning segmentation technique.

4. The image reconstruction system of claim 3, wherein the deep learning segmentation technique is any one of image segmentation and semantic segmentation.

5. The image reconstruction system of claim 2, wherein the sample 2D image generation unit performs operation by using an MIP technique.

6. The image reconstruction system of claim 2, wherein in the learning model construction unit, the training is performed using a Generative Adversarial Network (GAN) model.

7. The image reconstruction system of claim 1, wherein the MIP image conversion unit comprises:

a data input unit configured such that the target 2D X-ray image and the sample 2D image are input thereto; and an MIP learning unit configured such that the target 2D X-ray image and sample 2D image input to the data input unit are input to the learning model, and thus, the target 2D MIP image is generated.

8. The image reconstruction system of claim 7, wherein in the MIP learning unit, the input target 2D X-ray image is generated as the target 2D MIP image by an MIP technique.

9. The image reconstruction system of claim 7, wherein in the MIP learning unit, the training is performed using a Cycle GAN model.

10. An image reconstruction method that is performed by a control server having a database and a computation function and outputs a three-dimensional (3D) synthesized image from a two-dimensional (2D) X-ray image based on artificial intelligence, the image reconstruction method comprising:

step S100 configured such that in an artificial intelligence learning unit, a correct answer 3D image in which bones are segmented and extracted is generated from a sample 3D computed tomography (CT) image, a sample 2D image is generated from the correct answer 3D image, a sample 3D synthesized image is generated from the 2D image, and an artificial intelligence learning model is constructed as the generated sample 3D synthesized image is learned by being compared with the correct answer 3D image;

step S200 configured such that in a Maximum Intensity Projection (MIP) image conversion unit, an input target 2D X-ray image and the sample 2D image are input to a preset learning model, and thus, a target 2D MIP image is generated; and step S300 configured such that in a final 3D synthesized image output unit, the target 2D MIP image generated in the MIP image conversion unit is input to the learning model constructed in the artificial intelligence learning unit, and thus, a final 3D synthesized image is output.

11. The image reconstruction method of claim 10, wherein step S100 comprises:

step S110 configured such that in a data input unit, the sample 3D CT image is input thereto;

step S120 configured such that in a bone segmentation and extraction unit, the correct answer 3D image in which bones are segmented, extracted and reconstructed is generated from the input sample 3D CT image;

step S130 configured such that in a sample 2D image generation unit, the sample 2D image is generated from the correct answer 3D image generated in the bone segmentation and extraction unit; and step S140 configured such that in a learning model construction unit, the sample 3D synthesized image is generated from the sample 2D image generated in the sample 2D image generation unit and the artificial intelligence learning model is constructed as the generated sample 3D synthesized image is learned by being compared with the correct answer 3D image.

12. The image reconstruction method of claim 11, wherein step S120 is performed using a deep learning segmentation technique.

13. The image reconstruction method of claim 12, wherein the deep learning segmentation technique is any one of image segmentation and semantic segmentation.

14. The image reconstruction method of claim 11, wherein step S130 is performed using an MIP technique.

15. The image reconstruction method of claim 11, wherein in step S140, the training is performed using a Generative Adversarial Network (GAN) model.

16. The image reconstruction method of claim 10, wherein step S200 comprises:

step S210 configured such that in a data input unit, the target 2D X-ray image and the sample 2D image are input thereto; and step S210 configured such that in an MIP learning unit, the target 2D X-ray image and sample 2D image input to the data input unit are input to the learning model, and thus, the target 2D MIP image is generated.

17. The image reconstruction method of claim 16, wherein in step S220, the input target 2D X-ray image is generated as the target 2D MIP image by an MIP technique.

18. The image reconstruction method of claim 16, wherein in step S220, the training is performed using a Cycle GAN model.

19. A computer program stored in a non-transitory computer-readable storage medium to cause a computer to execute the image reconstruction method of outputting a three-dimensional (3D) synthesized image from a two-dimensional (2D) X-ray image based on artificial intelligence, set forth in claim 10, in combination with hardware.

* * * * *